(12) United States Patent
Schofield et al.

(10) Patent No.: US 12,313,641 B2
(45) Date of Patent: May 27, 2025

(54) METHOD OF OPERATING AN ANALYTICAL LABORATORY

(71) Applicant: Roche Diagnostics Operations, Inc., Indianapolis, IN (US)

(72) Inventors: Christopher Schofield, Rotkreuz (CH); Daniel Arnold, Merenschwand (CH); Moritz von Hopffgarten, Heidelberg (DE); Werner Smit, Hagendorn (CH); Chye Yin Priscillia Tan, Ibach (CH); Florian Reinhard Rauscher, Rotkreuz (CH); Angelos Chotzidis, Stuttgart (DE); Carlos Fernándes Gulias, Barcelona (ES)

(73) Assignee: ROCHE DIAGNOSTICS OPERATIONS, INC., Indianapolis, IN (US)

( * ) Notice: Subject to any disclaimer, the term of this patent is extended or adjusted under 35 U.S.C. 154(b) by 551 days.

(21) Appl. No.: 16/751,767

(22) Filed: Jan. 24, 2020

(65) Prior Publication Data

US 2020/0264200 A1    Aug. 20, 2020

(30) Foreign Application Priority Data

Feb. 15, 2019    (EP) .................................... 19157355

(51) Int. Cl.
*G01N 35/00*    (2006.01)

(52) U.S. Cl.
CPC ... *G01N 35/0092* (2013.01); *G01N 35/00732* (2013.01); *G01N 2035/00752* (2013.01); *G01N 2035/0094* (2013.01)

(58) Field of Classification Search
CPC ......... G01N 35/0092; G01N 35/00732; G01N 2035/0094; G01N 2035/00752
See application file for complete search history.

(56) References Cited

U.S. PATENT DOCUMENTS 6,581,012 B1 *   6/2003   Aryev ............. G05B 19/41865
                                                              702/22
2009/0130765 A1   5/2009   Bauer et al.
(Continued)

FOREIGN PATENT DOCUMENTS

EP    1248170 A1    10/2002
EP    3410323 A1    12/2018
(Continued)

OTHER PUBLICATIONS

Office Action issued Dec. 27, 2023, in Japanese Application No. 2020-023034, 6 pp. (English translation).

*Primary Examiner* — Matthew D Krcha
*Assistant Examiner* — Tingchen Shi
(74) *Attorney, Agent, or Firm* — Lee & Hayes, P.C.

(57) ABSTRACT

A method of operating an analytical laboratory is disclosed. The method comprises receiving and identifying sample containers and sorting them into a sample rack, retrieving an order list A comprising test orders corresponding to the sample containers within the sample rack, determining an optimal transportation route for the sample rack based on the order list A, a set of constraints and an objective function, the optimal transportation route being indicative of a list and/or sequence of laboratory instrument(s) required to complete the order list A, re-determining the optimal transportation route upon a change of the constraint(s) and/or of the objective function, transporting the sample rack to one or more of the laboratory instruments according to the optimal transportation route by the sample transportation system, and processing the biological samples according to the corresponding test orders by the target laboratory instrument(s).

18 Claims, 7 Drawing Sheets

(56) References Cited

U.S. PATENT DOCUMENTS

| | | | |
|---|---|---|---|
| 2011/0160899 A1 | 6/2011 | Tatsutani et al. | |
| 2014/0129172 A1* | 5/2014 | Eberhardt | G01N 35/0092 |
| | | | 702/108 |
| 2014/0305227 A1* | 10/2014 | Johns | B04B 13/00 |
| | | | 73/863.01 |
| 2016/0299164 A1* | 10/2016 | Ackermann | G01N 35/00693 |
| 2016/0341751 A1* | 11/2016 | Huber | G01N 35/00584 |
| 2018/0180635 A1 | 6/2018 | Lapham et al. | |
| 2018/0340949 A1* | 11/2018 | Maetzler | G01N 35/00732 |

FOREIGN PATENT DOCUMENTS

| | | |
|---|---|---|
| JP | 2013-072783 A | 4/2013 |
| JP | 2013-178161 A | 9/2013 |
| WO | 2001/009618 A1 | 2/2001 |
| WO | 2013/070756 A2 | 5/2013 |

\* cited by examiner

METHOD OF OPERATING AN ANALYTICAL LABORATORY

CROSS-REFERENCE TO RELATED APPLICATIONS

This application claims the benefit of EP 19157355.9, filed Feb. 15, 2019, which is hereby incorporated by reference.

BACKGROUND

The present disclosure generally relates to a computer-implemented method of operating an analytical laboratory, in particular an in-vitro diagnostic laboratory.

In vitro diagnostic testing has a major effect on clinical decisions, providing physicians with pivotal information. In analytical laboratories, in particular, in-vitro diagnostic laboratories, a multitude of analyses on biological samples are executed by laboratory instruments in order to determine physiological and biochemical states of patients, which can be indicative of a disease, nutrition habits, drug effectiveness, organ function and the like.

According to established laboratory procedures in complex analytical laboratories, a plurality of instruments process biological samples according to test orders, each test order defining one or more processing steps to be carried out on the biological sample. After the biological sample has been received and identified by a pre-analytical laboratory instrument, a control unit retrieves the corresponding test orders and determines which instruments (referred hereafter as target instrument(s)) are required to process the biological sample according to the test order(s). Having identified the target instrument(s), the control unit determines a sample workflow for each sample according to the test order(s). The sample workflow comprising a transportation route being indicative of a list and/or sequence of laboratory instrument(s) required to complete one or more of the test orders. Thereafter, the control unit instructs a sample transportation system to transport the biological samples to the target laboratory instrument(s) and instructs these to process the biological sample according to the test orders.

However, it has been observed that, at certain times, significant delays occur from receipt to processing of the biological sample by analytical laboratories. Such delays considerably affect the turn-around time of biological samples, that is the time between receipt of biological samples and completion of the corresponding test order(s). In addition, it has been observed that some laboratory instruments of the analytical laboratory are, at times, not being used to their full capabilities (throughput) while other laboratory instruments are overloaded.

The delays between receipt and processing of the biological sample by analytical laboratories are sometimes caused by sub-optimal routing of biological samples within the analytical laboratory, i.e., between the various laboratory instruments. One particular cause for sub-optimal routing of biological samples has been identified to be a change in the state of the analytical laboratory during transportation of biological samples that is between determination of the sample workflow and the actual processing of the biological samples by the various laboratory instruments.

Finding an optimal sample transportation route is an even more complex task in analytical laboratories where the biological samples are transported by the transportation system in sample racks for transporting multiple sample holders (tubes) at a time. In such cases, the transportation route of the sample rack must take into account the test orders of all biological samples in the same sample rack.

In known analytical laboratories, the route of a complete sample rack is determined at a point before the sample rack enters the transportation system. Hence, a change of the route as a reaction to a change of the laboratory status (e.g., instruments become unavailable) or individual sample events (e.g., a result was measured that triggers additional testing) cannot be taken into account to change the route of the sample rack. Furthermore, certain analytical laboratories comprise a sample transportation system, which has a limited number of transportation routes configured (configurable). The limited number of transportation routes may be due to physical or logical constraints of a sample transportation system and poses a limitation to the flexibility of routing samples since the number of optimal routes covering a wide range of situations might be higher than the number of routes that may be configured on the transportation system.

The consequence of such a limitation are longer turnaround times for samples, reduced test throughput on analytical instruments (because samples might visit analytical instruments where no analytic process is necessary). This indicates a serious limitation in the scalability of analytical laboratories.

The state of the analytical laboratory comprises (but is not limited to): availability of the laboratory instruments (including availability of consumables and validity of quality control values), current workload of the laboratory instruments (including eventual backlog or even an overload/rack jam), order demographics and sample history (e.g., previous results), processing status of samples on laboratory instruments when the biological sample holder is already back on the sample transportation system, and/or open and unprocessed test orders on each sample on a rack and the places where these requests could be processed.

Hence, there is a need for a method of operating an analytical laboratory such as, for example, an analytical laboratory system, to provide reduced and/or predictable Turn-Around-Times (TAT) for processing biological samples transported in sample racks and to optimally use the resources of the laboratory instruments.

SUMMARY

According to the present disclosure, a method of operating an analytical laboratory is presented. The method can comprise receiving and identifying a plurality of biological samples held in sample containers and sorting the plurality of sample containers into a sample rack by a pre-analytical laboratory instrument of the analytical laboratory and retrieving an order list A from a storage unit. The order list A can comprise a plurality of test orders corresponding to the sample containers within the respective sample rack. Each test order can define at least one processing step to be carried out on the biological sample held in the respective sample container. The method can also comprise determining an optimal transportation route by the control unit for the sample rack based on the order list A, a set of constraints and an objective function. The transportation route can be indicative of a list and/or sequence of laboratory instrument(s) required to complete one or more of the test orders of the order list A. The method can also comprise re-determining the optimal transportation route by the control unit upon a change of one or more of the set of constraints and/or a change of the objective function, transporting the sample rack to one or more of the plurality of laboratory instruments according to the optimal transportation route by the sample transportation system, and processing the biological samples according to the corresponding test orders by the target laboratory instrument(s).

Accordingly, it is a feature of the embodiments of the present disclosure to provide for a method of operating an analytical laboratory such as, for example, an analytical laboratory system, to provide reduced and/or predictable Turn-Around-Times (TAT) for processing biological samples transported in sample racks and to optimally use the resources of the laboratory instruments. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
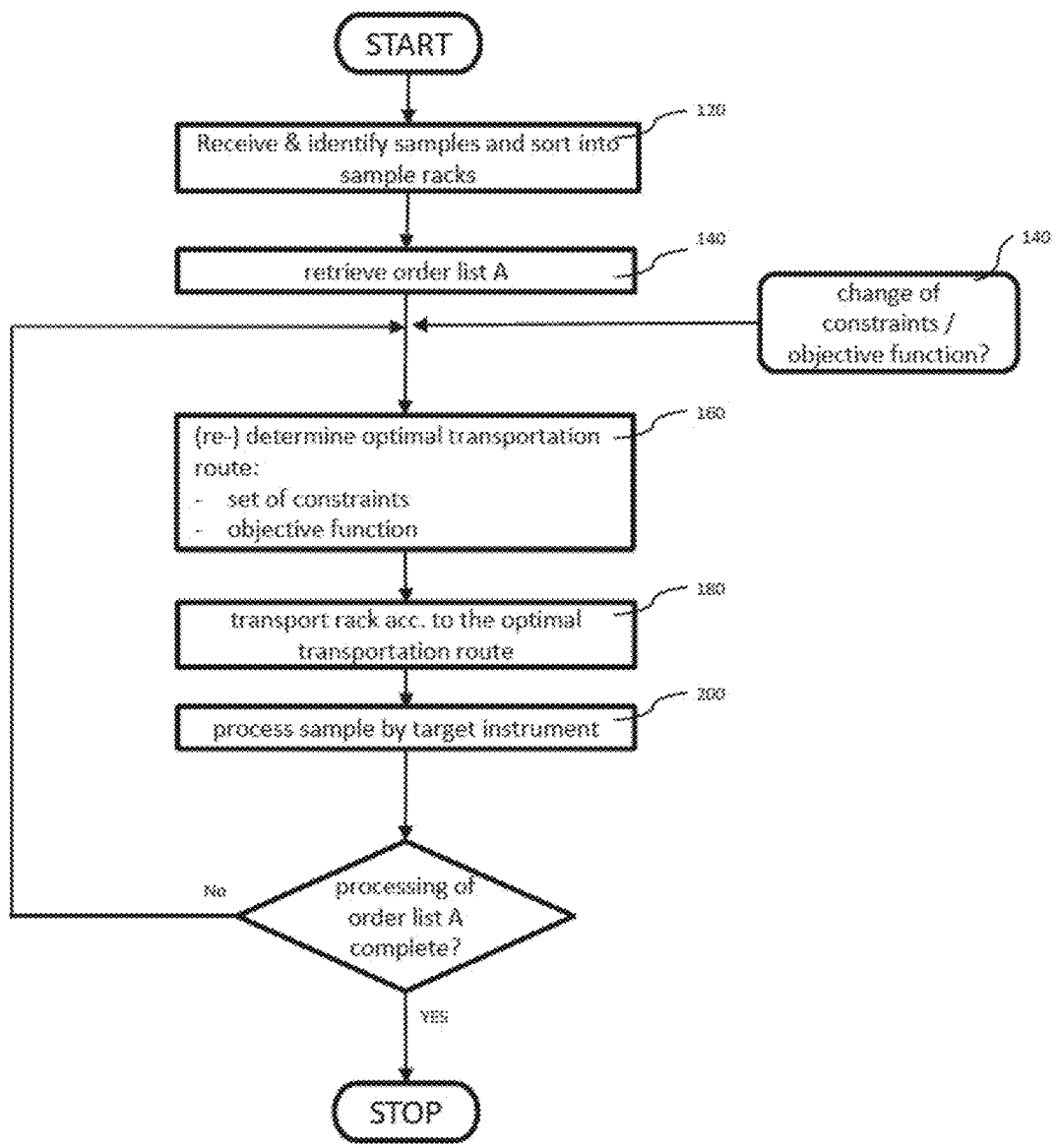
FIG. 1 illustrates a flowchart illustrating a method of operating an analytical laboratory according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

Disclosed herein is a method of operating an analytical laboratory. The method can comprise the steps of: a) receiving and identifying a plurality of biological samples held in sample containers and sorting the plurality of sample containers into a sample rack by a pre-analytical laboratory instrument of the analytical laboratory; b) retrieving an order list A from a storage unit, the order list A comprising a plurality of test orders corresponding to the sample containers within the respective sample rack; each test order defining at least one processing step to be carried out on the biological sample held in the respective sample container; c) determining an optimal transportation route by the control unit for the sample rack based on the order list A, a set of constraints and an objective function, the optimal transportation route being indicative of a list and/or sequence of laboratory instrument(s) required to complete one or more of the test orders of the order list A; d) re-determining the optimal transportation route by the control unit upon a change of one or more of the set of constraints and/or a change of the objective function; e) transporting the sample rack to one or more of the plurality of laboratory instruments according to the optimal transportation route by the sample transportation system; and f) processing the biological samples according to the corresponding test orders by the target laboratory instrument(s).

According to some embodiments, steps d) to f) can be repeated iteratively if the complete order list A cannot be processed by within a single transportation route.

Embodiments disclosed herein can be advantageous for several reasons. On one hand, the optimal transportation route can be dynamically (re)determined and, hence, can adapt to any change in the analytical laboratory—as reflected by the set of constraints.

On the other hand, since the optimal transportation route is determined as a global optimum over all sample containers of a rack, an overall optimum can be achieved as compared to a collection of individually optimal routes for each sample container. Individually optimal routes (for each sample container) can bear the risk that the rack is sent back and forth between instruments. Therefore, a holistic view of all sample containers of a rack can be of great advantage.

The global optimum transportation route can be determined by considering target laboratory instruments for each sample container, narrowing down the list of potential workflows by eliminating routes that conflict with one or more of the set of constraints. The term 'conflicts' can be understood in this context in the sense that the respective transportation route does not meet one or more of the constraints.

Finally, an optimal transportation route can be determined, which can achieve a highest value of an objective function. In this way, the optimal transportation route may not only be dynamic in the sense that it can adapt to any change in the analytical laboratory, but can be determined in view of an objective function that can be custom tailored to the laboratory needs. Even more, the optimal transportation route can be (re)determined also when such objectives change.

For example, there can be times of day (e.g., daytime) when the main objective of an analytical laboratory is to complete all test orders in the shortest time possible. However, there can be times of day (e.g., nighttime) when the main objective of an analytical laboratory is to complete all test orders with the least amount of consumables or the lowest number of instruments, so that some instruments can be turned off (or switched into a low power mode). In such cases, the processing time can be of lower importance.

Further embodiments disclosed herein address the limitation of certain analytical laboratories comprising a sample transportation system, which can have a limited number of transportation routes configured (configurable). The limited number of transportation routes may be due to physical or logical constraints of a sample transportation system. In order to nevertheless achieve the targets of the analytical laboratory, as defined by the objective function, the step of determining the optimal transportation route can comprise the steps of: i) retrieving (from a storage unit or from a storage of the transportation system) a route list B of all available transportation routes of the sample transportation system, ii) determining a route instrument list C for each transportation route of the route list B, the route instrument list C comprising laboratory instruments reachable by the respective transportation route; iii) determining an instrument list D of all laboratory instruments required to process all sample containers within the respective sample rack according to the order list A; iv) discarding from the route list B any transportation route(s) that does not contain any laboratory instrument(s) of the instrument list D; and v) determining the optimum transportation route from route list B by the objective function.

Certain terms will be used, the formulation of which should not be interpreted to be limited by the specific term chosen, but to relate to the general concept behind the specific term.

The terms 'sample', 'patient sample' and 'biological sample' can refer to material(s) that may potentially contain an analyte of interest. The patient sample can be derived from any biological source, such as a physiological fluid, including blood, saliva, ocular lens fluid, cerebrospinal fluid, sweat, urine, stool, semen, milk, ascites fluid, mucous, synovial fluid, peritoneal fluid, amniotic fluid, tissue, cultured cells, or the like. The patient sample can be pretreated prior to use, such as preparing plasma from blood, diluting viscous fluids, lysis or the like. Methods of treatment can involve filtration, distillation, concentration, inactivation of interfering components, and the addition of reagents. A patient sample may be used directly as obtained from the source or used following a pretreatment to modify the character of the sample. In some embodiments, an initially solid or semi-solid biological material can be rendered liquid by dissolving or suspending it with a suitable liquid medium. In some embodiments, the sample can be suspected to contain a certain antigen or nucleic acid.

The term 'analyte' can be a component of a sample to be analyzed, e.g., molecules of various sizes, ions, proteins, metabolites and the like. Information gathered on an analyte may be used to evaluate the impact of the administration of drugs on the organism or on particular tissues or to make a diagnosis. Thus, 'analyte' can be a general term for substances for which information about presence, absence and/or concentration is intended. Examples of analytes are e.g., glucose, coagulation parameters, endogenic proteins (e.g., proteins released from the heart muscle), metabolites, nucleic acids and so on.

The term 'analysis or 'analytical test' as used herein can encompass a laboratory procedure characterizing a parameter of a biological sample for qualitatively assessing or quantitatively measuring the presence or amount or the functional activity of an analyte.

The term 'reagent' as used herein can refer to materials necessary for performing an analysis of analytes, including reagents for sample preparation, control reagents, reagents for reacting with the analyte to obtain a detectable signal, and/or reagents necessary for detecting the analyte. Such reagents may include reagents for isolating an analyte and/or reagents for processing a sample and/or reagents for reacting with an analyte to obtain a detectable signal and/or washing reagents and/or diluents.

The terms 'sample container', 'sample holder' and 'sample tube' can refer to any individual container for storing, transporting, and/or processing a sample. In particular, the term without limitation refers to a piece of laboratory glass- or plastic-ware optionally comprising a cap on its upper end. The container comprises an opening for dispensing/aspirating liquid into respectively out of the vessel. The opening may be closed by a cap, a breakable seal or like suitable means for closing the opening in a liquid-tight manner. Sample tubes, e.g. sample tubes used to collect blood, often comprise additional substances such as clot activators or anticoagulant substances, which have an impact on the processing of the sample. Consequently, different tube types typically are adapted for pre-analytical and analytical requirements of a particular analysis, e.g. a clinical chemistry analysis, a hematological analysis or a coagulation analysis. A mix up of sample tube types can make (blood) samples unusable for analysis. To prevent errors in the collection and handling of samples, the sample caps of many tube manufacturers are encoded according to a fixed and uniform color scheme. Some sample tube types in addition or alternatively are characterized by particular tube dimensions, cap dimensions, and/or tube color. A dimension of a tube comprises e.g. its height, its size and/or further characteristic shape properties. Sample containers are identified using identification tag(s) attached thereto. The term 'identification tag' as used herein refers to an optical and/or radio frequency based identifier that allows the identifier tag to be uniquely identified by a corresponding identification tag reader.

The 'identification tag' may comprise, but is not limited to, a barcode, a QR code or an RFID tag.

The term 'sample carrier' as used herein can refer to any kind of holder configured to receive one or more sample tubes and configured to be used for transporting sample tube(s). Sample carriers may be of two major types, single holders and sample racks.

A 'single holder' can be a type of sample carrier configured to receive and transport a single sample tube. Typically, a single holder can be provided as a puck, i.e., a flat cylindrical object with an opening to receive and retain a single sample tube.

A 'sample rack' can be a type of sample carrier, typically made of plastics and/or metal, adapted for receiving, holding and transporting a plurality of sample tubes, e.g., five or more sample tubes e.g., disposed in one or more rows. Apertures, windows, or slits may be present to enable visual or optical inspection or reading of the sample tubes or of the samples in the sample tubes or of a label, such as a barcode, present on the sample tubes held in the sample rack.

The term 'laboratory instrument' as used herein can encompass any apparatus, or apparatus component, operable to execute one or more processing steps/workflow steps on one or more biological samples and/or one or more reagents. The expression 'processing steps' thereby can refer to physically executed processing steps such as centrifugation, aliquotation, sample analysis and the like. The term 'instrument' can cover pre-analytical instruments, post-analytical instruments, and, also, analytical instruments.

The term 'analyzer'/'analytical instrument' as used herein can encompass any apparatus, or apparatus component, configured to obtain a measurement value. An analyzer can be operable to determine via various chemical, biological, physical, optical or other technical procedures a parameter value of the sample or a component thereof. An analyzer may be operable to measure the parameter of the sample or of at least one analyte and return the obtained measurement value. The list of possible analysis results returned by the analyzer can comprise, without limitation, concentrations of the analyte in the sample, a digital (yes or no) result indicating the existence of the analyte in the sample (corresponding to a concentration above the detection level), optical parameters, DNA or RNA sequences, data obtained from mass spectrometry of proteins or metabolites and physical or chemical parameters of various types. An analytical instrument may comprise units assisting with the pipetting, dosing, and mixing of samples and/or reagents. The analyzer may comprise a reagent-holding unit for holding reagents to perform the assays. Reagents may be arranged, for example, in the form of containers or cassettes containing individual reagents or group of reagents, placed in appropriate receptacles or positions within a storage compartment or conveyor. It may comprise a consumable feeding unit. The analyzer may comprise a process and detection system whose workflow can be optimized for certain types of analysis. Examples of such analyzer can be clinical chemistry analyzers, coagulation chemistry analyzers, immunochemistry analyzers, urine analyzers, nucleic acid analyzers, used to detect the result of chemical or biological reactions or to monitor the progress of chemical or biological reactions.

The term 'pre-analytical instrument' as used herein can encompass any apparatus, or apparatus component, that is configured to perform one or more pre-analytical processing steps/workflow steps comprising, but not limited to, centrifugation, resuspension (e.g., by mixing or vortexing), capping, decapping, recapping, sorting, tube type identification, sample quality determination and/or aliquotation steps. The processing steps may also comprise adding chemicals or buffers to a sample, concentrating a sample, incubating a sample, and the like.

The term 'post-analytical instrument' as used herein can encompass any apparatus, or apparatus component, that is configured to perform one or more post-analytical processing steps/workflow steps comprising, but not limited to, sample unloading, transport, recapping, decapping, temporary storage/buffering, archiving (refrigerated or not), retrieval and/or disposal.

The term 'sample transportation system' as used herein can encompass any apparatus, or apparatus component, that is configured to transport sample carriers (each holding one or more sample containers) between laboratory instruments. In particular, the sample transportation system can be a one-dimensional conveyor-belt based system, a two-dimensional transportation system (such as a magnetic sample carrier transport system) or a combination thereof.

The term 'control unit' as used herein can encompass any physical or virtual processing device configurable to control a laboratory instrument or system comprising one or more laboratory instruments in a way that workflow(s) and workflow step(s) can be conducted by the laboratory instrument/system. The control unit may, for example, instruct the laboratory instrument/system to conduct pre-analytical, post analytical and analytical workflow(s)/workflow step(s). The control unit may receive information from a data management unit regarding which steps need to be performed with a certain sample. In some embodiments, the control unit may be integral with a data management unit, may be comprised by a server computer and/or be part of one laboratory instrument or even distributed across multiple instruments of the analytical laboratory. The control unit may, for instance, be embodied as a programmable logic controller running a computer-readable program provided with instructions to perform operations.

A 'storage unit' or 'database' can be a computing unit for storing and managing data such as a memory, hard disk or cloud storage. This may involve data relating to biological sample(s) to be processed by the automated system. The data management unit may be connected to an LIS (laboratory information system) and/or an HIS (hospital information system). The data management unit can be a unit within or co-located with a laboratory instrument. It may be part of the control unit. Alternatively, the database may be a unit remotely located. For instance, it may be embodied in a computer connected via a communication network.

The term 'communication network' as used herein can encompass any type of wireless network, such as a WiFi™, GSM™, UMTS or other wireless digital network or a cable based network, such as Ethernet™ or the like. In particular, the communication network can implement the Internet protocol (IP). For example, the communication network can comprise a combination of cable-based and wireless networks.

An 'analytical laboratory' as used herein can comprise a control unit operatively coupled to one or more analytical pre- and post-analytical work cells wherein the control unit can be operable to control the instruments. In addition, the control unit may be operable to evaluate and/or process gathered analysis data, to control the loading, storing and/or unloading of samples to and/or from any one of the analyzers, to initialize an analysis or hardware or software operations of the analysis system used for preparing the samples, sample tubes or reagents for said analysis and the like. In particular, the instruments of an analytical laboratory and the control unit can be interconnected by a communication network.

A 'test order' as used herein can encompass any data object, computer loadable data structure, modulated data representing such data being indicative of one or more processing steps to be executed on a particular biological sample. For example, a test order may be a file or an entry in a database. A test order can indicate an analytical test if, for example, the test order comprises or is stored in association with an identifier of an analytical test to be executed on a particular sample.

A 'STAT sample' can be a sample which may need to be processed and analyzed urgently as the analysis result may be of life-crucial importance for a patient.

FIG. 1 shows a flowchart illustrating a first embodiment of a method of operating an analytical laboratory. According to the method, in a first step 120, sample containers holding biological sample(s) can be received and identified by a pre-analytical laboratory instrument of the analytical laboratory. The identification can be performed, for example, by an identifier tag reader reading an identifier tag attached to the sample container holding the biological sample. Once identified, the sample containers can be sorted into sample racks such as, for example, by a robotic arm. Common sample racks hold five or more sample tubes. Sample tubes sorted into a sample rack are associated with the respective sample rack, for example in the form of a look-up table of a database. This allows the control unit to determine which sample containers are in a sample rack by merely identifying the sample rack (e.g. by reading a sample rack identifier such as a rack barcode) instead of having to repeatedly identify each sample container. Nevertheless, depending on the applicable regulations, instruments—in particular analytical instruments—still identify each and every biological sample container and do not rely on the sample container—rack association.

In a subsequent step 140, an order list A can be retrieved from a database. The order list A can comprise one or more test order(s) defining at least one processing step to be carried out on each biological sample in the sample rack.

Once the order list A has been retrieved, in step 160, the control unit can determine the optimal transportation route based on the order list A, a set of constraints and an objective function. The term 'transportation route' as used herein can refer to a list and/or sequence of laboratory instruments to which a sample rack can be transported. A transportation route can be indicative of a physical and/or logical route of a sample transportation system, connecting two or more laboratory instruments. According to some embodiments, a laboratory route can comprise a list and/or sequence of laboratory instruments to which the route can connect. The term 'connect' in this context can be understood that the sample transportation system can be configured to transport a sample rack according to a transportation route to a position in the proximity of a laboratory instrument, a position which can enable the laboratory instrument to process biological samples in the respective sample rack. According to some embodiments, the sample rack can be transported either directly into the laboratory instruments and/or to a sample rack loading unit which can transfer the sample rack into the laboratory instruments and/or to a close proximity of a laboratory instrument which can be capable to handle biological samples directly from a sample rack located on a transportation system.

The physical route can define a transportation route in 1, 2 or 3 spatial dimensions, while a logical route can define a route by a sequence of logical locations of a sample transportation system, such as sample rack loading position nr. X, sample rack turning table nr. X, conveyor belt nr. X.

According to some embodiments, in addition to the sequence of laboratory instruments to which a sample rack is transported, the optimal transportation route can further comprise the timing according to which the sample rack is to be transported to the respective instruments. For example, the timing can be of great importance if the biological sample first needs to be prepared by a pre-analytical instrument and must be processed by an analytical instrument immediately thereafter. Another example can be when the biological sample needs to spend a very specific amount of time in a pre-analytical instrument such as an incubator or centrifuge to ensure proper sample preparation for an analytical instrument. Furthermore, the timing of the processing can also relevant in view of sample degradation which can often be correlated with its processing time, especially when the sample is outside of a temperature controlled area, in which case the sample can be transferred to a post-analytical instrument such as a temperature-controlled archiving unit after a certain amount of time. Another example can be when certain processing steps such as, for example, certain rarely performed analytical tests are performed relatively rarely in an analytical laboratory. In such cases, embodiments of the disclosed method/system can align the timing of transporting the sample rack to an instrument with a schedule of tests performed by the analytical laboratory in order to avoid that the respective analytical test cannot be performed for an extended period of time. Timing of processing of the targets can also be of great importance in view of the validity of quality control and/or calibration of certain laboratory instruments such as, for example, analytical instruments.

At the occurrence of any change of the one or more of the set of constraints and/or a change of the objective function, the optimal transportation route can be re-determined.

In a following step 180, the sample transportation system can transport the sample rack to one or more of the plurality of laboratory instruments according to the optimal transportation route. The sample transportation system can either request the optimal transportation route from the control unit upon a sample rack being placed on the transportation system (pull approach) and/or the control unit can instruct the sample transportation system (push approach). According to further embodiments, the sample transportation system can request the optimal transportation route from the control unit upon a sample rack being identified by an identifier reader unit of the transport system.

In step 200, the target laboratory instrument(s) can process the biological sample according to the corresponding test order. The target laboratory instrument(s) can process the biological samples upon the sample rack being transported thereto. The laboratory instruments can either request the test order corresponding to the sample rack upon its receipt from the control (pull approach) and/or can be instructed by the control unit to process the biological samples according to respective test orders of the order list A (push approach).

According to some embodiments, the step of processing the biological sample according to the test order by the target laboratory instrument(s) can comprise determining the presence, absence and/or concentration of one or more analyte(s) in the biological sample such as, for example, by analytical laboratory instrument(s).

Figure 2:
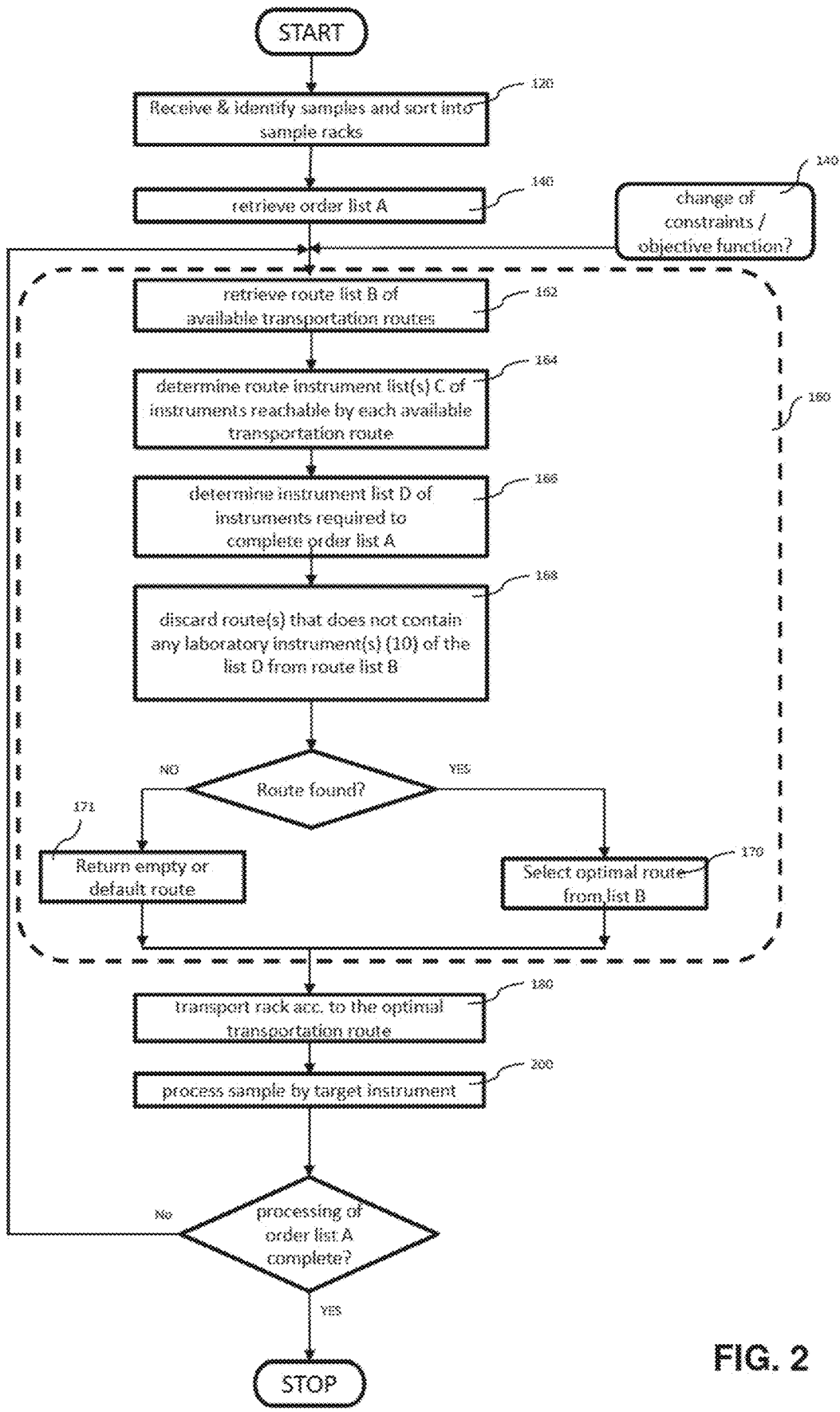
FIG. 2 illustrates a flowchart illustrating a method according to another embodiment of the present disclosure.
Figure 3:
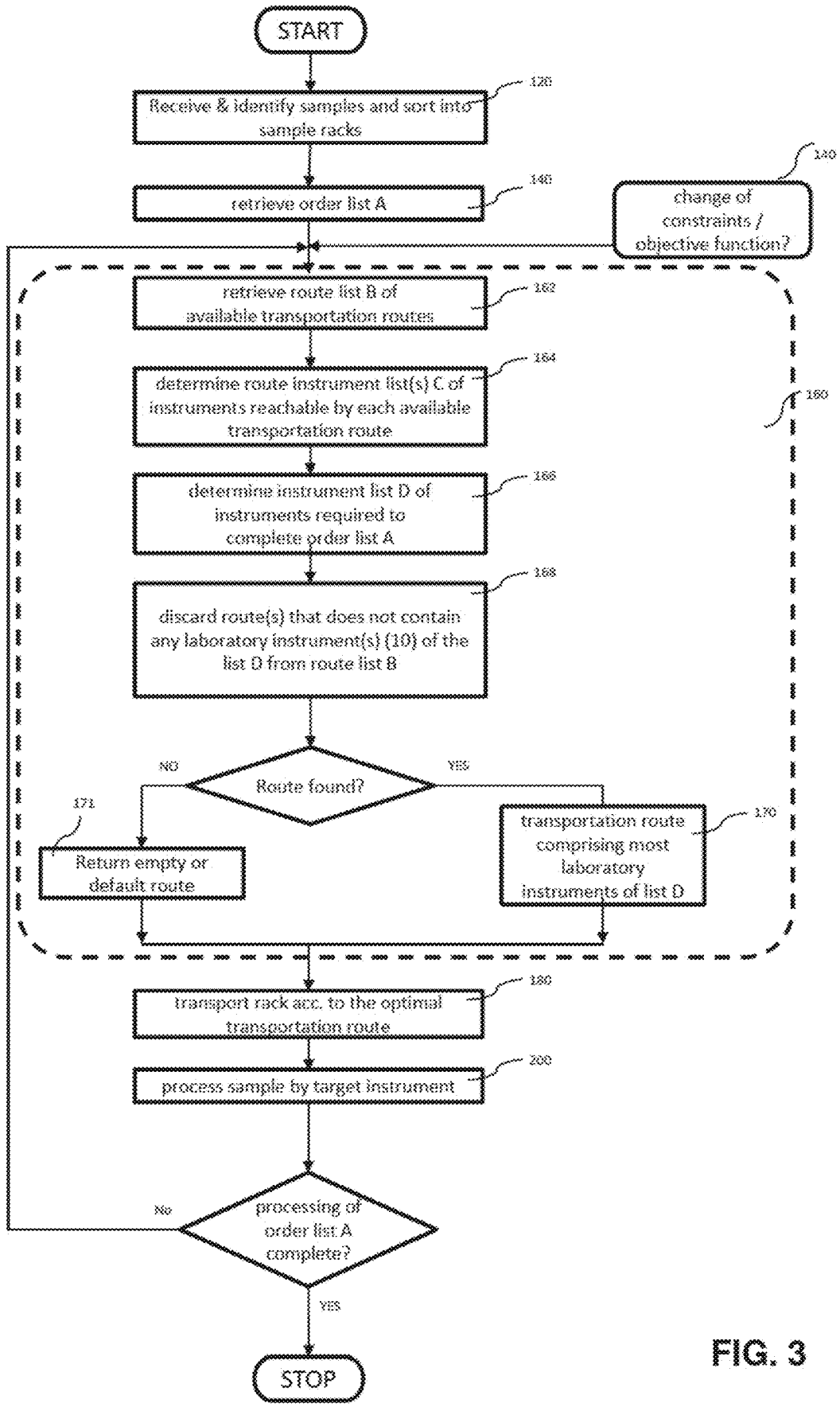
FIG. 3 illustrates a flowchart illustrating a method according to a further embodiment of the present disclosure.
Figure 4:
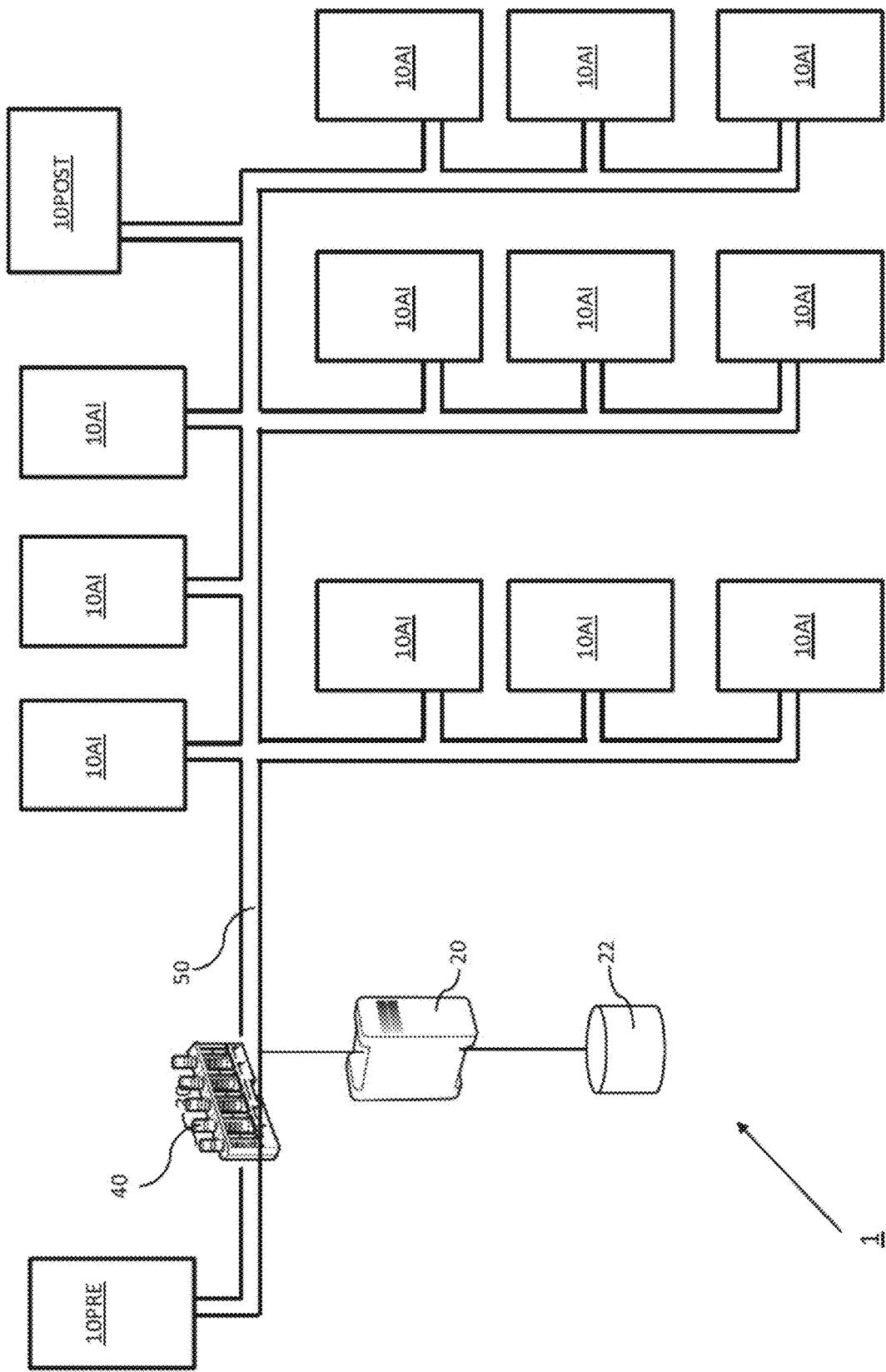
FIG. 4 illustrates a highly schematic block diagram of an analytical laboratory according to an embodiment of the present disclosure.

Different embodiments of (re) determining the optimal transportation route will be now described in relation to FIGS. 2-4.

FIG. 2 shows a flowchart according to some embodiments, which can be particularly advantageous for analytical laboratories comprising a sample transportation system with a defined set of available transportation routes. Side note: the step 160 of determining respectively re-determining the optimal transportation route is delimited on FIGS. 2 and 3 by a rounded rectangle drawn with dashed lines.

As shown on FIG. 3, the step of determining and/or re-determining the optimal transportation route by the control unit can comprise, in a step 162, the control unit can retrieve a route list B comprising all available transportation routes of the sample transportation system 50. In this context, the term 'available' can refer to a transportation route according to which the sample transportation system 50 can currently transport a sample rack. Any transportation route comprising a section/part/target instrument, which is blocked, off-line, masked, contaminated and/or being serviced can be considered unavailable.

In a subsequent step 164, the control unit can determine one or more route instrument list(s) C for each transportation route of the route list B. The route instrument list C can comprise laboratory instruments reachable by the respective transportation route. In this step, the laboratory instruments each route can serve can be extracted.

In a subsequent step 166, the control unit can determine an instrument list D of all laboratory instruments required to process all sample containers within the respective sample rack according to the order list A. Step 166 can comprise two substeps. In the first substep, target laboratory instruments can be determined for each of the test order(s) which can be configured to carry out the at least one processing step according to the test order. This step can be performed in view of instruments of the analytical laboratory, which are currently available. The term 'available'—in the context of the present application—can be understood to comprise one or more of the following: the analytical instrument is switched on and not in a low power mode; all modules of the analytical instrument required to carry out the respective test order are operational, all consumables required to carry out the respective test order are available, and/or all quality control and/or calibration steps required before carrying out the respective test order are available, are up-to-date and valid. In summary, an instrument can be considered available if it can complete the respective test order.

In the second substep of step 166, the lists of instruments needed to process the biological samples in each sample tube of the sample rack can be consolidated into an instrument list D. As a result of this consolidation, the instrument list D can comprise all instruments required by any test order for any test tube in the sample rack. Duplicates can be omitted since a sample rack needs to be transported to an instrument only once per rack (not multiple times for each sample tube).

In a subsequent step 168, any transportation route(s) of route list B that does not contain any laboratory instrument(s) of the instrument list D can be discarded. In other words, transportations routes which do not reach any instrument, which could process at least one test order for any of the sample tubes of the sample rack, are "useless" in this respect and therefore discarded.

In step 170, the optimal transportation route from route list B can be determined by the objective function.

If no route is found, then, in step 171, an empty or default route can be determined as the globally optimal transportation route. The default route may for example comprise a transportation route directly to a post analytical instrument, where the biological samples can be stored, until a change occurs which can result in a new globally optimal transportation route being determined. The so-called empty route can instruct the sample transportation system to keep the sample rack at its current location, for example, in a temporary buffer. Alternatively, or additionally, a manually configured transportation route may be selected.

FIG. 3 illustrates a further embodiment of the steps of determining and/or re-determining the optimal transportation route, wherein the objective function can determine an optimum transportation route, the transportation route from route list B which can comprise most laboratory instruments of instrument list D.

According to further embodiments, if in step 170 more than one routes can be found with the same highest number of laboratory instruments of instrument list D, then the fastest route can be determined as the globally optimal transportation route in subsequent step 172. The term 'fastest' can refer either the shortest transportation time of a sample rack by the sample transportation system or the shortest estimated processing time of all biological samples by all laboratory instruments of the respective transportation route. For example, two routes 1 and 2 can both comprise three instruments from the instrument D. Route 1 can comprise instruments a, b and c while route 2 can comprise instruments a, b and d. Both instruments c and d can perform the same test order of a biological sample, but instrument c can perform the test order faster (e.g., either because it is a faster instrument or because it has a lower workload). In this case, transportation route 1 can be selected as globally optimal transportation route, because it has the shortest estimated total processing time of all test orders of all sample tubes of the sample rack. In a further embodiment, the term 'fastest' can refer merely to the lowest total number of instruments of a particular transportation route.

According to further embodiments, if in step 172 more than one route can be determined to be the fastest (i.e., with identical estimated processing times) then the transportation with highest priority can be determined as the globally optimal transportation route in subsequent step 174. Depending on use cases of analytical laboratories, certain transportation routes can be preferred/recommended over other—otherwise equally optimal—transportation routes.

The optimal transportation route can be determined and re-determined based on the order list A related to all samples in a sample rack, a set of constraints and an objective function. The optimal transportation route can be indicative of a list and/or sequence of and/or transportation route to all laboratory instrument(s) required to complete the order list A. Completion of the test order list A can refer to completion of all processing steps of all test orders related to all sample tubes of the sample rack.

According to some embodiments, the set of constraints considered for determining an optimal transportation route by the control unit can comprises one or more of the following:

Availability and/or prioritization of the laboratory instruments to complete any of the processing steps according to the test orders of the order list A—The availability of laboratory instruments can be a criterion for exclusion, i.e., an unavailable instrument may not be considered for the selection of an optimal transportation route. The availability of laboratory instruments can comprises the following aspects: determining the target laboratory instrument is powered on and not in a low-power mode; determining whether all modules of the target laboratory instrument required to carry out the respective test order are operational; determining whether all consumables required to carry out the respective test order are available; and/or determining whether all quality control and/or calibration values of the target laboratory instrument are up-to-date and valid. The prioritization of the laboratory instruments can be a constraint that prioritizes one instrument over another when both are suitable to complete a test order.

Workload of the laboratory instruments—the workload can be a constraint similar to prioritization, but may not be fixed. Instead, the workload of an instrument can change over time. Based on the Workload of the laboratory instruments, the (re)determination method can chose an instrument—and corresponding transportation route—with a lower workload.

Processing status of the biological samples within the sample containers within the respective sample rack—The processing status of one of the biological samples within a rack can be a limiting constraint in a sense that, depending on the configuration of the specific embodiment, laboratory instruments may not be considered for determining an optimal transportation route, if a test order corresponding to one of the samples in the rack is being processed and/or has been processed by the respective laboratory instrument.

Location of the sample rack within the sample transportation system—depending on the configuration of the specific embodiment, the current location of the sample rack within the sample transportation system can act as a limiting constraint on the availability of transportations routes. Therefore, as part of (re)determining the optimal transportation route, the control unit can determine which transport routes are available from that location. In addition to availability of transportation routes, also the transportation time of the sample rack on the sample transportation system can be dependent on the current location of the sample rack.

Order demographics of the test orders of the order list A—in certain use cases, the demographics (gender, age, race, and the like) can have an impact on the selection or prioritization of a laboratory instrument over the other and hence of one transportation route over the other. For example, reference values of certain analytical tests can be dependent on the order demographics such as adults vs. children, male vs. female patients.

Availability and/or prioritization of each transportation route of the sample transportation system to transport the sample rack to a plurality of laboratory instruments—any transportation route comprising a section/part/target instrument which is blocked, off-line, masked, contaminated and/or being serviced can be considered unavailable and can act as a limiting constrain on the determination of the optimal transportation route.

Urgency/priority of one or more of the test orders of the order list A—certain samples may need to be processed and analyzed very urgently as the analysis result may be of life-crucial importance for a patient. Hence, the method of determining respectively re-determining the optimal transportation route can prioritize transportation routes, which comprise a laboratory instrument, which can carry out urgent test orders related to any of the biological samples in the respective sample rack.

Rules to resolve conflicts between equally optimal transportation routes—for the case where several equally optimal transportation routes are found, some embodiments can comprise a set of rules to select one of equally optimal routes. Such rules may comprise a default route or comprise a workload-balancing rule configured to ensure balanced workload of the laboratory instruments by alternatively selecting each of equally optimal transportation routes.

Add-on test orders following the completion of any of the test orders of the order list A, comprising repeat, rerun or reflex test orders—in addition to the order list A, add-on test orders related to any of the biological samples in the sample rack can be considered by the method for determining respectively re-determining the optimal transportation route.

According to some embodiments, instead of a single criterion (e.g., fastest route, most instruments on the route), the optimal transportation route can be determined (based on the order list A, a set of constraints and an objective function) using a scoring function such as, for example, a weighted scoring function of one or more of the following criteria: most completed test orders of the order list A related to each of the plurality of sample containers within the sample rack, shortest aggregated processing time of the test orders of the order list A, shortest processing time of urgent test orders of the order list A, least aggregated amount of consumable used by the target laboratory instruments required to complete the order list A, most efficient and/or balanced utilization of the laboratory instruments, shortest and/or quickest transportation route of the sample rack on the sample transportation system, and/or lowest aggregated risk of contamination of any one of the biological samples held in each of the plurality of sample containers within the sample rack.

For example, each of the above criteria can be assigned a score of 1 or 0, wherein 1 attributed to a route which satisfies the criteria and 0 to one that does not. In a scoring function, the scores for each criteria can be summed up for all routes and the route with the highest score can be selected as the optimal transportation route. According to further embodiments, a weighted scoring function can be used, wherein certain criteria can be considered more important (higher weighing) than others.

According to further embodiments, the step of determining and/or re-determining the optimal transportation route by the control unit can further comprises the step of removing transportation route(s) from route list B that can comprise at least one laboratory instrument from a list of disallowed instruments E. In a particular use case, an instrument can be disallowed for a specific biological sample because the same sample has been already processed by the same instrument and an add-on test (repeat, rerun or reflex test) should not be performed on the same instrument.

According to further embodiments, the step of determining and/or re-determining the optimal transportation route by the control unit can further comprise the step of removing transportation route(s) from route list B which do not comprise all laboratory instrument(s) from a list of compulsory instruments F. In a particular use case, an instrument can be compulsory for a specific biological sample, for example, because the same must be processed by a particular instrument due to regulatory and/or operational reasons.

FIG. 4 shows a highly schematic block diagram of an embodiment of the disclosed analytical laboratory 1. As shown on the block diagram of FIG. 6, embodiments of the disclosed analytical laboratory 1 for processing biological sample(s) can comprise a plurality of laboratory instruments 10 and a control unit 20 communicatively connected by a communication network. The plurality of laboratory instruments 10 can be configured to execute processing steps on the biological samples according to instructions from the control unit 20. In the present disclosure, reference numeral 10 can be used to collectively refer to all laboratory instruments, comprising pre-analytical laboratory instruments 10PRE, analytical laboratory instrument 10AI and/or post-analytical laboratory instruments 10POST.

The pre-analytical instruments 10PRE comprised by the analytical laboratory 1 may be one or more from the list comprising: an instrument for centrifugation of samples, a capping-, decapping- or recapping instrument, aliquoter, a buffer to temporarily store biological samples or aliquots thereof.

The post-analytical instruments 10POST comprised by the analytical laboratory 1 may be one or more from the list comprising: a recapper, an unloader for unloading a sample from an analytical system and/or transporting the sample to a storage unit or to a unit for collecting biological waste.

According to various embodiments of the disclosed analytical laboratory 1, the plurality of laboratory instruments 10 may be identical or different instruments such as clinical- & immunochemistry analyzers, coagulation chemistry analyzers, immunochemistry analyzers, urine analyzers, nucleic acid analyzers, hematology instruments and the like.

The control unit 20 can be configured to control the laboratory system 1 to carry out the steps of one or more of the methods herein disclosed and can be communicatively connected to the storage unit 22.

As shown in FIG. 4, the analytical laboratory 1 can further comprise a sample transportation system 50 interconnecting the plurality of laboratory instruments 10. According to some embodiments, the sample transportation system 50 can be a one-dimensional conveyor-belt based system. According to further embodiments disclosed (but not illustrated), the sample transportation system 50 can be a two-dimensional transportation system (such as a magnetic sample carrier transport system).

Figure 5:
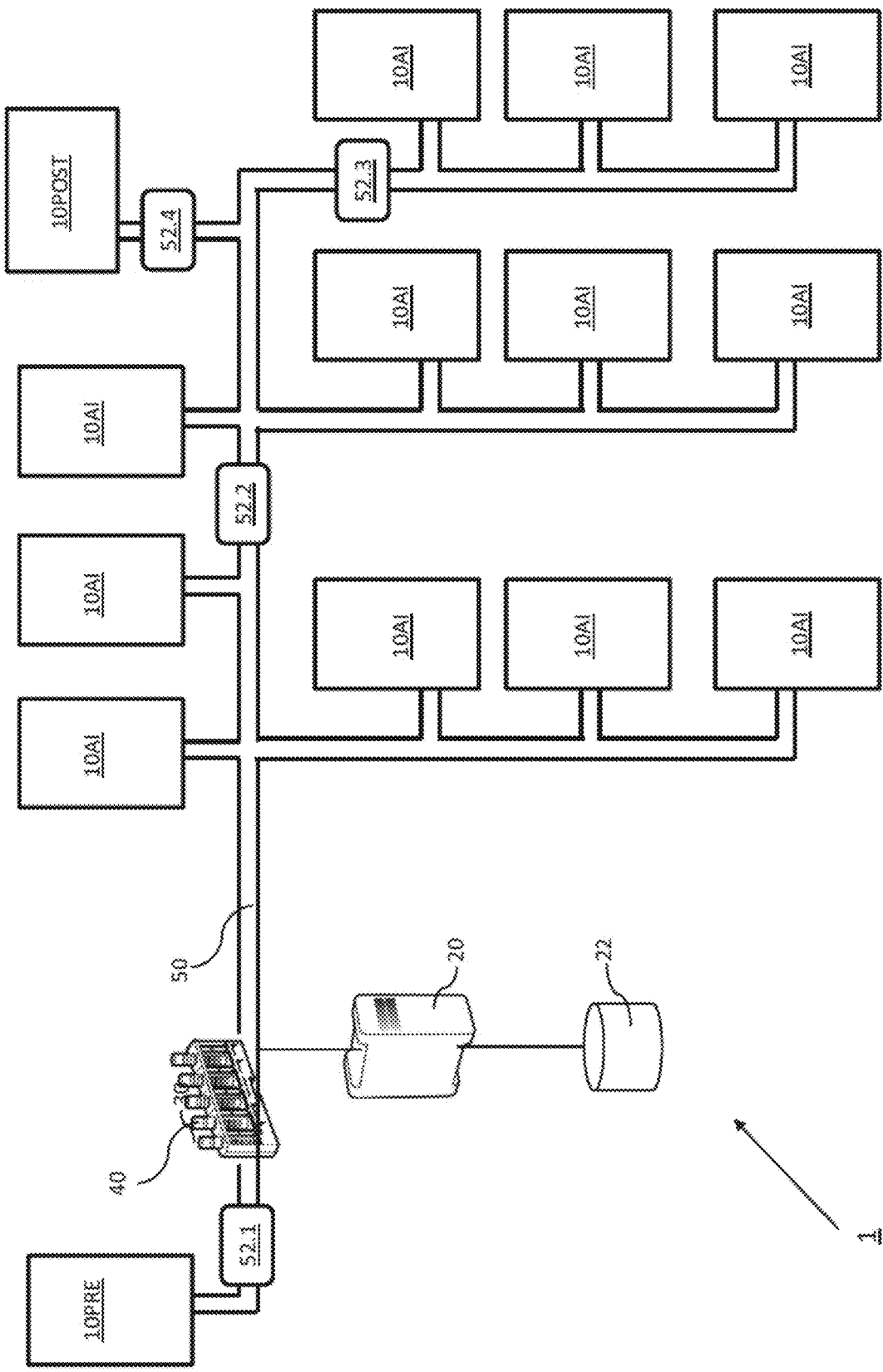
FIG. 5 illustrates a highly schematic block diagram of an analytical laboratory according to another embodiment of the present disclosure.

FIG. 5 shows a further embodiment of the analytical laboratory 1, further comprising a plurality of identifier reader units 52 of the sample transportation system 50, strategically placed at locations of the sample transportation system 50, where the sample racks 40 can be identified in order to request a re-determination of the optimal transportation route.

The identifier reader units 52 of the sample transportation system 50 are also known as address extension units or smart boxes.

According to some embodiments comprising identifier reader units 52, the route list B of all available transportation routes of the sample transportation system 50 can be determined in view of a current location of the respective sample rack 40. The current location of the respective sample rack 40 can be indicative of one of the laboratory instruments 10, the sample transportation system 50 and/or the identifier reader unit 52 of the sample transportation system 50. As apparent from FIG. 5, depending on the location of a sample rack 40, with respect to one of the identifier reader units 52, different transportation routes can be available.

In a first use case, an identifier reader unit 52.1 can be arranged after a pre-analytical laboratory instrument 10PRE so that the optimal transportation route can be (re) determined after biological samples of a sample rack 40 have been prepared for analysis.

In a second use case, an identifier reader unit 52.2 can be arranged 'after' a certain number of different transportation routes in order to overcome limitations on the number Nmax of transportation routes configurable on the transportation system 50. In this respect, the identifier reader unit 52.2 can divide the transportation system 50 into sections, each identifier reader unit 52.2 enabling a further number of Nmax transportation routes that a sample rack 40 can be transported along.

In a third use case, an identifier reader unit 52.3 can be arranged on a transportation route before a plurality of identical or similar analytical laboratory instruments 10AI in order to enable load balancing by (re) determining the optimal transportation route dynamically right before the sample rack 40 can reach one of the identical or similar analytical laboratory instruments 10AI.

In a fourth use case, an identifier reader unit 52.4 can be arranged in the proximity of a post-analytical laboratory instrument 10POST in order to achieve optimal add-on testing. Add-on testing can comprise repeat testing, rerun testing and/or reflex testing of biological sample(s), which, following completion of the respective test order(s), can be stored in a post-analytical laboratory instrument 10POST. The term 'repeat testing' can refer to repeating the same analytical test under exactly the same conditions to confirm an analytical result. The term 'rerun testing' can refer to running the same analytical test, but under different conditions (such as, for example, a different dilution of the sample) due to an out-of-range analytical result. The term 'reflex testing' can refer to performing a different analytical test triggered by an analytical result (e.g., antibody-antigen testing).

In the context of the arrangement of the identifier reader unit, the terms 'after' and 'before' can be understood with reference to the common transportation sequence on a sample transportation system predominantly from pre-analytical laboratory instrument(s) 10PRE to analytical laboratory instruments 10AI and finally to post-analytical laboratory instrument(s) 10POST.

Turning now to FIGS. 6-9, particular embodiments of the laboratory instruments 10PRE, 10POST, 10AI are described.

Figure 6:
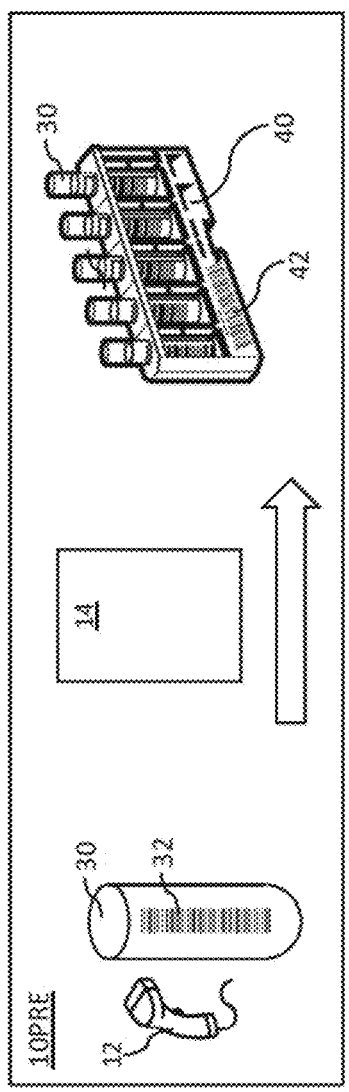
FIG. 6 illustrates a highly schematic block diagram of a pre-analytical laboratory instrument of the laboratory system according to an embodiment of the present disclosure.

FIG. 6 shows a pre-analytical laboratory instrument 10PRE comprising a sample container-sorting unit 14 configured to sort sample containers 30 holding biological samples into sample racks 40. Each sample rack 40 can be identified by a rack identifier of a rack tag 42 attached to the sample rack 40. The pre-analytical laboratory instruments 10PRE can be further configured to transmit signals to the laboratory control unit associating the sample identifier(s) ID of sorted sample containers 30 with the sample rack identifier(s) of the corresponding sample rack(s) 40. For embodiments where a pre-analytical laboratory instrument 10PRE sorts sample containers 30 into sample racks 40, one or more analytical laboratory instruments can further be configured to read the rack identifier Rack-ID from the rack tag 42 and transmit said rack identifier Rack-ID to the laboratory control unit with the test query.

Figure 7:
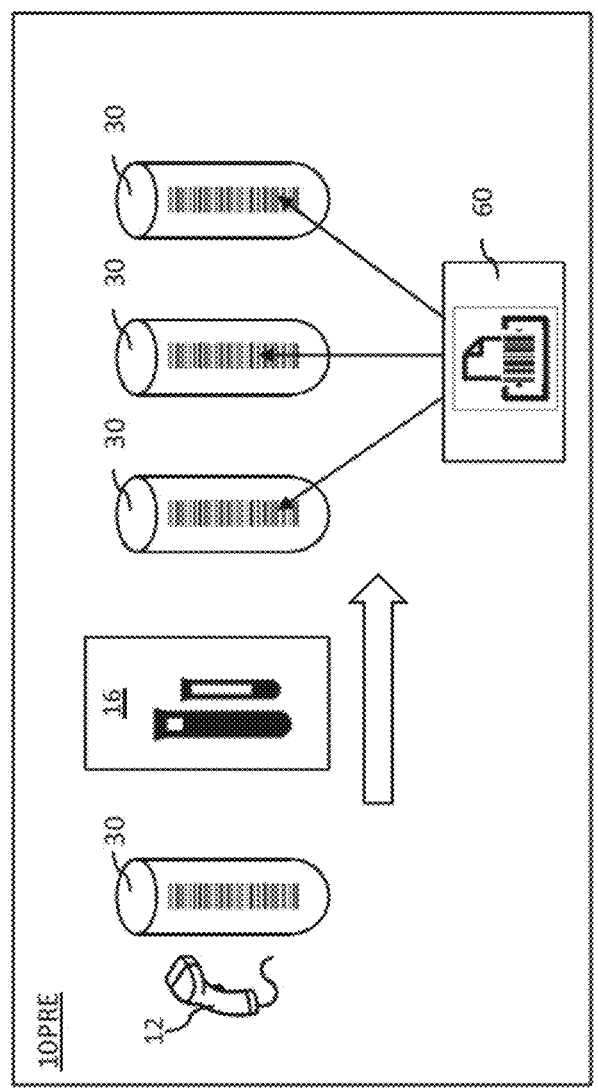
FIG. 7 illustrates a highly schematic block diagram of a pre-analytical laboratory instrument of the laboratory system according to another embodiment of the present disclosure.

FIG. 7 shows a further embodiment of a pre-analytical laboratory instrument 10PRE, comprising an aliquoting unit 16 configured to prepare aliquots of biological sample(s) from the sample container(s) 30 and provide each of said aliquots with a sample identifier ID on an identifier tag 32 by an identifier tag writer 60.

Figure 8:
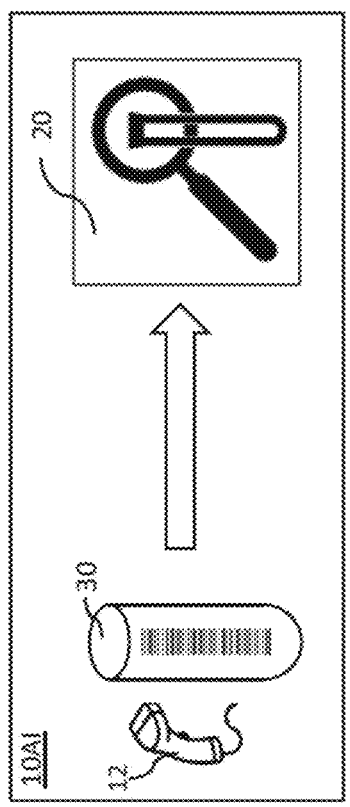
FIG. 8 illustrates a highly schematic block diagram of an analytical laboratory instrument of the laboratory system according to an embodiment of the present disclosure.

FIG. 8 shows an embodiment of an analytical laboratory instrument 10AI, comprising an analytical unit 18 configured to carry out an analytical test to measure the presence, absence and/or concentration of at least one analyte in the biological sample. The analytical laboratory instrument 10AI can perform analytical test(s) of the biological sample in response to the test order(s).

Figure 9:
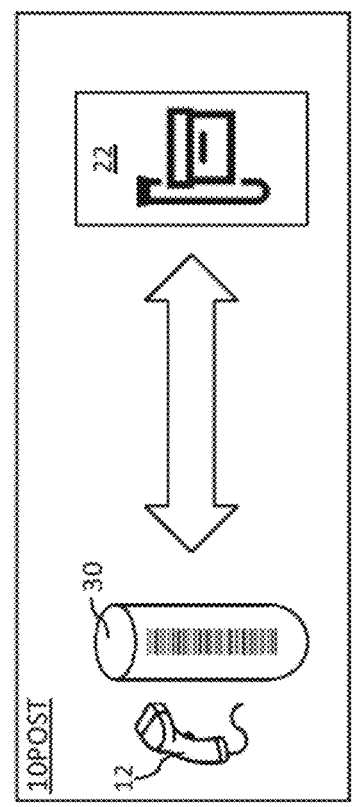
FIG. 9 illustrates a highly schematic block diagram of a post-analytical laboratory instrument of the laboratory system according to an embodiment of the present disclosure.

FIG. 9 shows an embodiment of a post-analytical laboratory instrument 10POST comprising a storage unit 19. The post-analytical laboratory instrument 10AI can be configured to store respectively retrieve sample containers 30 into respectively from the storage unit 19. The query by post-analytical laboratory instrument(s) 10POST to the laboratory control unit for a processing order can comprise a container to store respectively retrieve into respectively from the storage unit 19. Correspondingly, when queried by a post-analytical laboratory instrument 10POST, the control unit can transmit data indicative of a sample container 30 to be retrieved from the storage unit 19. In response to the data indicative of a sample container 30 to be stored respectively retrieved, the post-analytical laboratory instrument 10POST can store respectively retrieves the sample container 30 from the storage unit 19.

Further disclosed and proposed is a computer program product including computer-executable instructions for performing the disclosed method in one or more of the embodiments enclosed herein when the program can be executed on a computer or computer network. Specifically, the computer program may be stored on a computer-readable data carrier or a server computer. Thus, specifically, one, more than one or even all of method steps as indicated above may be performed by using a computer or a computer network, preferably by using a computer program.

As used herein, a computer program product can refer to the program as a tradable product. The product may generally exist in any format, such as in a downloadable file, on a computer-readable data carrier on premise or located at a remote location (cloud). Specifically, the computer program product may be distributed over a data network (such as a cloud environment). Furthermore, not only the computer program product, but also the execution hardware may be located on premised or in a cloud environment.

Further disclosed and proposed can be a computer-readable medium comprising instructions which, when executed by a computer system, can cause an analytical laboratory to perform the method according to one or more of the embodiments disclosed herein.

Further disclosed and proposed is a modulated data signal comprising instructions which, when executed by a computer system, can cause an analytical laboratory to perform the method according to one or more of the embodiments disclosed herein.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A method of operating an analytical laboratory, the method comprising:
   receiving a plurality of biological samples in sample containers arranged into a sample rack;
   receiving a plurality of test orders corresponding to the plurality of sample containers within the respective sample rack, each of the plurality of test orders identifying at least one processing step to be carried out on the biological sample in the respective sample container;
   determining, by a control unit, an optimal transportation route within a transportation system for processing the biological samples using a plurality of laboratory instruments distributed in the transportation system, wherein the optimal transportation route is determined based on the plurality of test orders, using a scoring function configured to optimize two or more criteria for processing all of the plurality of biological samples in the sample rack;
   transporting the sample rack to the plurality of laboratory instruments according to the determined optimal transportation route by the transportation system; and
   processing the biological samples according to the corresponding test orders by the plurality of laboratory instruments.

2. The method of operating an analytical laboratory according to claim 1, further comprising:
   determining, by the control unit, an updated optimal transportation route, using the scoring function, in response to any of the plurality of sample containers being identified by an identifier reader unit of the transportation system.

3. The method of operating an analytical laboratory according to claim 1, wherein determining the optimal transportation route by the control unit comprises:
   determining, using the scoring function, a first optimal transportation route;
   determining, based on the plurality of biological samples, a disallowed laboratory instrument;
   based on determining that the disallowed laboratory instrument is associated with the first optimal transportation route, using the scoring function to determine a different second optimal transportation route.

4. The method of operating an analytical laboratory according to claim 1, wherein determining the optimal transportation route by the control unit comprises:
   determining, using the scoring function, a first optimal transportation route;
   determining, based on the plurality of biological samples, a compulsory laboratory instrument;
   based on determining that the compulsory laboratory instrument is not associated with the first optimal transportation route, using the scoring function to determine a different second optimal transportation route.

5. The method of operating an analytical laboratory according to claim 1, wherein determining the optimal transportation route comprises:
   determining a current location of the sample rack, wherein the current location of the sample rack is indicative of one of the laboratory instruments or the or an identifier reader unit of the transportation system; and
   providing the current location as an input to the scoring function.

6. The method of operating an analytical laboratory according to claim 1, wherein processing the biological samples comprises determining a concentration of one or more analyte(s) in a first biological sample.

7. The method of claim 1, wherein the scoring function is configured to optimize the two or more criteria with respect to processing all of the plurality of biological samples, wherein a first criteria comprises minimizing an aggregate processing time.

8. The method of claim 1, wherein the scoring function is configured to optimize the two or more criteria with respect to processing all of the plurality of biological samples, wherein a first criteria comprises minimizing an aggregate amount of consumable used by the laboratory instruments.

9. The method of claim 1, wherein the scoring function is configured to optimize the two or more criteria with respect to processing all of the plurality of biological samples, wherein a first criteria comprises optimizing an aggregate balanced use of the laboratory instruments.

10. The method of claim 1, wherein the scoring function is configured to optimize the two or more criteria with respect to processing all of the plurality of biological samples, wherein a first criteria comprises minimizing an aggregate length of the optimal transportation route.

11. The method of claim 1, wherein the scoring function is configured to optimize the two or more criteria with respect to processing all of the plurality of biological samples, wherein a first criteria comprises minimizing an aggregate risk of contamination.

12. The method of claim 1, wherein the scoring function is configured to optimize the two or more criteria with respect to processing all of the plurality of biological samples, wherein a first criteria comprises minimizing power consumption by the plurality of laboratory instruments.

13. The method of claim 1, wherein the scoring function is configured to optimize the two or more criteria with respect to processing all of the plurality of biological samples, wherein a first criteria comprises maximizing throughput of the plurality of test orders.

14. A transportation system for an analytical laboratory, the transportation system comprising:
   a control unit communicatively connected to a plurality of laboratory instruments, the control unit being configured to perform operations comprising:

receiving a plurality of biological samples in sample containers arranged into a sample rack;

receiving a plurality of test orders corresponding to the plurality of sample containers within the sample rack, each of the plurality of test orders identifying at least one processing step to be carried out on the biological sample in the respective sample container;

determining, by a control unit, an optimal transportation route within a transportation system for processing the biological samples using the plurality of laboratory instruments distributed in the transportation system, wherein the optimal transportation route is determined based on the plurality of test orders, using a scoring function configured to optimize two or more criteria for processing all of the plurality of biological samples in the sample rack;

transporting the sample rack to the plurality of laboratory instruments according to the determined optimal transportation route by the transportation system; and processing the biological samples according to the corresponding test orders by the plurality of laboratory instruments.

15. The transportation system according to claim 14, wherein the plurality of laboratory instruments comprise one or more analytical laboratory instruments configured to carry out one or more analytical processing steps on the biological samples to determine a concentration of analyte(s) in a first biological sample.

16. The transportation system according to claim 14, wherein the plurality of laboratory instruments comprise one or more post-analytical laboratory instrument(s) configured to perform one or more from a list comprising: recapping, unloading, disposing and archiving of biological sample(s).

17. The transportation system according to claim 14, wherein the transportation system comprises an identifier reader unit configured to identify the sample rack and/or any one the plurality of sample containers, the identifier reader unit being communicatively connected to the control unit.

18. A non-transitory computer-readable medium storing instructions thereon which, when executed by a control unit of an analytical laboratory cause the control unit to perform operations comprising:

receiving a plurality of biological samples in sample containers arranged into a sample rack;

receiving a plurality of test orders corresponding to the plurality of sample containers within the sample rack, each of the plurality of test orders identifying at least one processing step to be carried out on the biological sample in the respective sample container;

determining, by a control unit, an optimal transportation route within a transportation system for processing the biological samples using a plurality of laboratory instruments distributed in the transportation system, wherein the optimal transportation route is determined based on the plurality of test orders, using a scoring function configured to optimize two or more criteria for processing all of the plurality of biological samples in the sample rack;

transporting the sample rack to the plurality of laboratory instruments according to the determined optimal transportation route by the transportation system; and processing the biological samples according to the corresponding test orders by the plurality of laboratory instruments.

* * * * *